United States Patent
Ge et al.

(10) Patent No.: US 12,351,773 B2
(45) Date of Patent: Jul. 8, 2025

(54) LUBRICIOUS THERMOPLASTIC COMPOUNDS AND THERMOPLASTIC ARTICLES MADE THEREFROM

(71) Applicant: Avient Corporation, Avon Lake, OH (US)

(72) Inventors: Qing Ge, Solon, OH (US); Jing Liu, Avon, OH (US)

(73) Assignee: Avient Corporation, Avon Lake, OH (US)

( * ) Notice: Subject to any disclaimer, the term of this patent is extended or adjusted under 35 U.S.C. 154(b) by 850 days.

(21) Appl. No.: 17/422,363

(22) PCT Filed: Jan. 7, 2020

(86) PCT No.: PCT/US2020/012544
§ 371 (c)(1),
(2) Date: Jul. 12, 2021

(87) PCT Pub. No.: WO2020/150044
PCT Pub. Date: Jul. 23, 2020

(65) Prior Publication Data
US 2022/0119724 A1    Apr. 21, 2022

Related U.S. Application Data

(60) Provisional application No. 62/792,497, filed on Jan. 15, 2019.

(51) Int. Cl.
| | |
|---|---|
| C10M 107/44 | (2006.01) |
| A61L 29/08 | (2006.01) |
| C10M 107/34 | (2006.01) |
| C10M 107/42 | (2006.01) |
| C10M 125/22 | (2006.01) |
| C10M 169/04 | (2006.01) |
| C10N 40/00 | (2006.01) |
| C10N 50/08 | (2006.01) |

(52) U.S. Cl.
CPC ......... *C10M 107/44* (2013.01); *A61L 29/085* (2013.01); *C10M 107/34* (2013.01); *C10M 107/42* (2013.01); *C10M 125/22* (2013.01); *C10M 169/04* (2013.01); *C10M 2201/084* (2013.01); *C10M 2209/1045* (2013.01); *C10M 2217/0285* (2013.01); *C10M 2217/0443* (2013.01); *C10M 2217/0453* (2013.01); *C10N 2040/50* (2020.05); *C10N 2050/08* (2013.01)

(58) Field of Classification Search
CPC .......... C08L 75/00; C08L 75/04; C08L 75/06; C08L 75/08; C08L 75/10; C08L 75/12; C08L 75/14; C08L 75/16; C08L 39/06; C08F 26/10; C08F 26/06
See application file for complete search history.

(56) References Cited

U.S. PATENT DOCUMENTS

| | | | |
|---|---|---|---|
| 4,781,703 A * | 11/1988 | Walker | A61M 25/0014 604/533 |
| 4,883,699 A * | 11/1989 | Aniuk | C08L 101/00 525/123 |
| 5,001,009 A | 3/1991 | Whitbourne | |
| 5,061,424 A * | 10/1991 | Karimi | A61L 29/049 264/300 |
| 2002/0045049 A1* | 4/2002 | Madsen | C09D 5/14 524/400 |
| 2006/0240060 A1 | 10/2006 | Bavaro | |
| 2007/0287800 A1 | 12/2007 | Acquarulo et al. | |
| 2009/0041923 A1 | 2/2009 | Lin et al. | |
| 2010/0136073 A1 | 6/2010 | Preuss et al. | |
| 2010/0209472 A1* | 8/2010 | Wang | A61M 25/10 606/2 |
| 2010/0217186 A1 | 8/2010 | Nazarova et al. | |
| 2012/0046411 A1 | 2/2012 | Kulshrestha et al. | |
| 2012/0132457 A1 | 5/2012 | Tai et al. | |
| 2012/0322348 A1 | 12/2012 | Yokoi et al. | |

(Continued)

FOREIGN PATENT DOCUMENTS

| | | |
|---|---|---|
| CN | 101222946 A | 7/2008 |
| CN | 101883813 A | 11/2010 |

(Continued)

OTHER PUBLICATIONS

Technical Information, Aug. 2023, Kollidon, pp. 1-9 (Year: 2023).*
Kazmierska, K, et al., Determination of urethral catheter surface lubricity, Journal of Materials Science: Materials m Medicine, vol. 19, No. 6,, pp. 2301-2306, published 2008.
Pharmaceutical Polymer Materials, Gao Feng, East China University of Science and Technology Press, 2014. 10, first edition, p. 96, 2014.
Jin Chang et al., ,PU/PVP Study on hydrophilic lubricity of semi-interpenetrating networks; China, Plastics, No. 12, pp. 29-33; 1999.

(Continued)

*Primary Examiner* — Michael C Romanowski
*Assistant Examiner* — Thomas J Kessler
(74) *Attorney, Agent, or Firm* — Michael J. Sambrook; Emily E. Vlasek; David V. Monateri

(57) ABSTRACT

Lubricious thermoplastic articles are formed from thermoplastic compounds including (a) thermoplastic elastomer selected from thermoplastic polyurethane, polyether block amide, and combinations thereof; and (b) from about 5 to about 20 weight percent, by weight of the compound, of hydrophilic water-insoluble polymer selected from polyolefin-polyoxyalkylene block copolymer, crosslinked polyvinylpyrrolidone, and combinations thereof. The thermoplastic compounds are capable of providing enhanced lubricity in the thermoplastic articles without significant degradation in mechanical properties such as elongation and tensile strength, as compared to thermoplastic articles formed from the neat thermoplastic elastomer and subjected to the same heat processing history.

11 Claims, No Drawings

(56) References Cited

U.S. PATENT DOCUMENTS

| | | |
|---|---|---|
| 2015/0218354 A1 | 8/2015 | Kulshrestha et al. |
| 2016/0022877 A1* | 1/2016 | Gravesen .............. A61L 29/049 264/328.2 |
| 2016/0220735 A1* | 8/2016 | Frautschi ................. C08K 3/30 |
| 2018/0036516 A1 | 2/2018 | Wang |
| 2019/0224384 A1 | 7/2019 | Lundahl et al. |

FOREIGN PATENT DOCUMENTS

| | | |
|---|---|---|
| CN | 102438670 A | 5/2012 |
| CN | 102639160 A | 8/2012 |
| CN | 103041454 A | 4/2013 |
| CN | 107405430 A | 11/2017 |
| CN | 107698952 A | 2/2018 |
| CN | 108430528 A | 8/2018 |
| EP | 2174982 A2 | 4/2010 |
| EP | 2517828 A1 | 10/2012 |
| JP | 2011151352 A | 8/2011 |
| WO | 9858990 A1 | 12/1998 |
| WO | 2006032043 A2 | 3/2006 |

OTHER PUBLICATIONS

Office Action in Chinese Application No. 202080009044.4 dated Sep. 2, 2022 (providing concise explanation of Pharmaceutical Polymer Materials, Gao Feng, East China University of Science and Technology Press, 2014. 10, first edition, p. 96).

* cited by examiner

LUBRICIOUS THERMOPLASTIC COMPOUNDS AND THERMOPLASTIC ARTICLES MADE THEREFROM

CLAIM OF PRIORITY

This application claims the benefit of U.S. Provisional Patent Application Ser. No. 62/792,497 and filed on Jan. 15, 2019, which is hereby incorporated by reference in its entirety.

FIELD OF THE INVENTION

This invention relates to thermoplastic compounds which can be formed into thermoplastic articles having enhanced lubricity without significant degradation of desirable mechanical properties, which makes the thermoplastic compounds especially useful for making thermoplastic articles for biomedical applications such as catheters.

BACKGROUND OF THE INVENTION

Demand exists for medical devices such as catheters. Typically, catheters are made from polymeric materials that provide a combination of biological, chemical, and physical properties that are necessary or desirable for in vivo biomedical applications. Important properties include biocompatibility, anti-thrombogenicity, good mechanical properties, and ease of processing. Another important property is surface lubricity which allows a catheter to be easily inserted into and removed from the body.

Conventionally, increasing surface lubricity of catheters is provided by methods that involve applying a hydrophilic coating to the outer surface of a catheter or some other form of surface treatment. Such methods are problematic for at least two reasons. First, such methods are not cost effective because they involve a secondary process beyond the forming (e.g., by extrusion) of the catheter itself. Second, a coating applied to the surface of a catheter can exhibit poor durability and be susceptible to wearing off during processing, handling, and/or use of the catheter.

One attempt to provide increased surface lubricity in catheters by other than surface coating methods is described in United States Patent Appl. Pub. No. 2007/0287800 to Acquarulo et al. and assigned to Foster Corporation ("Foster"). Foster discloses lubricious polymer compounds that are blends of certain hydrophilic polymers, such as polyethylene glycol, and certain thermoplastic resin, such as thermoplastic polyurethane. Although Foster discloses such blends have a lower coefficient of friction than that of the base resin alone, Foster also teaches that, undesirably, certain mechanical properties of such blends are significantly worse than those mechanical properties of the base resin alone.

SUMMARY OF THE INVENTION

Consequently, a need exists for thermoplastic compounds that are capable of providing enhanced lubricity in thermoplastic articles such as catheters without the drawbacks of a secondary process or a surface coating, while also avoiding significant degradation in mechanical properties such as elongation and tensile strength.

The aforementioned needs are met by one or more aspects of the disclosed invention.

One aspect of the invention is lubricious thermoplastic articles formed from thermoplastic compounds including (a) thermoplastic elastomer selected from thermoplastic polyurethane, polyether block amide, and combinations thereof, and (b) from about 5 to about 20 weight percent, by weight of the compound, of hydrophilic water-insoluble polymer selected from polyolefin-polyoxyalkylene block copolymer, crosslinked polyvinylpyrrolidone, and combinations thereof.

Another aspect of the invention is methods of making the thermoplastic articles as disclosed herein for an intended use. The methods include the steps of: (a) providing ingredients including the thermoplastic elastomer and the hydrophilic water-insoluble polymer; (b) melt mixing the ingredients to provide the thermoplastic elastomer compound; and (c) forming the thermoplastic elastomer compound to provide the article for the intended use without a subsequent step of applying a lubricity enhancing agent to the article prior to the intended use.

Features of the invention will become apparent with reference to the following embodiments. There exist various refinements of the features noted in relation to the above-mentioned aspects of the disclosed invention. Additional features may also be incorporated in the above-mentioned aspects of the disclosed invention. These refinements and additional features may exist individually or in any combination. For instance, various features discussed below in relation to any of the described aspects of the invention may be incorporated into any of the described aspects of the invention alone or in any combination.

EMBODIMENTS OF THE INVENTION

In some embodiments, the invention is directed to thermoplastic compounds.

In other embodiments, the invention is directed to thermoplastic articles.

In further embodiments, the invention is directed to methods of making thermoplastic articles.

Required and optional features of these and other embodiments of the disclosed invention are described.

As used herein, the term "compound" means a composition or mixture resulting from melt mixing, or compounding, a neat polymer resin and at least one other ingredient including but not limited to one or more additives, or one or more other polymer resins, or both.

As used herein, the term "formed from" (including related terms such as "forming") means, with respect to an article (or component of an article) and a thermoplastic material, that the article (or component of the article) is extruded, molded, shaped, pressed, or otherwise made from the thermoplastic material under sufficient heating to enable such forming. As such, the term "formed from" (including related terms such as "forming") means, in some embodiments, the article (or component of an article) can comprise, consist essentially of, or consist of, the material; and, in other embodiments, the article (or component of an article) consists of the material because the article (or component of an article) is, for example, made by an extrusion process or a molding process.

As used herein, the term "free of" a certain component or substance means, in some embodiments, that no amount of that component or substance is intentionally present, and, in other embodiments, that no functionally effective amount of that component or substance is present, and, in further embodiments, that no amount of that component or substance is present.

As used herein, the term "Dynamic COF" means the dynamic coefficient of friction of a specimen under wetted conditions as determined according ASTM D1894.

As used herein, the term "Elongation at Break" means the percent elongation at break of a specimen as determined according to ASTM D412.

As used herein, the term "Hardness" means the hardness of a specimen as determined according to ASTM D2240. Hardness is reported as Shore A hardness unless specifically identified otherwise.

As used herein, the term, "Tensile Strength at Break" means the tensile strength at break of a specimen as determined according to ASTM D412.

As used herein, the term "Relative Dynamic COF" means the ratio of the Dynamic COF for a specimen thermoplastic article formed from a thermoplastic compound including a neat polymer resin and at least one other ingredient relative to the Dynamic COF for a control thermoplastic article formed from the neat polymer resin alone and subjected to the same heat processing history as the thermoplastic compound.

As used herein, the term "Relative Elongation at Break" means the ratio of the Elongation at Break for a specimen thermoplastic article formed from a thermoplastic compound including a neat polymer resin and at least one other ingredient relative to the Elongation at Break for a control thermoplastic articled formed from the neat polymer resin alone and subjected to the same heat processing history as the thermoplastic compound.

As used herein, the term "Relative Hardness" means the ratio of the Hardness for a specimen thermoplastic article formed from a thermoplastic compound including a neat polymer resin and at least one other ingredient relative to the Hardness for a control thermoplastic articled formed from the neat polymer resin alone and subjected to the same heat processing history as the thermoplastic compound.

As used herein, the term "Relative Tensile Strength at Break" means the ratio of the Tensile Strength at Break for a specimen thermoplastic compound including a neat polymer resin and at least one other ingredient relative to the Tensile Strength at Break for the neat polymer resin alone when subjected to the same heat processing history as the specimen thermoplastic compound.

Thermoplastic Articles Formed from Thermoplastic Compounds

Some aspects of the invention are directed to lubricious thermoplastic articles formed from thermoplastic compounds.

According to the invention, lubricious thermoplastic articles are formed from thermoplastic compounds including (a) thermoplastic elastomer selected from thermoplastic polyurethane, polyether block amide, and combinations thereof, and (b) from about 5 to about 20 weight percent, by weight of the compound, of hydrophilic water-insoluble polymer selected from polyolefin-polyoxyalkylene block copolymer, crosslinked polyvinylpyrrolidone, and combinations thereof.

The thermoplastic compounds are capable of providing enhanced lubricity in the thermoplastic articles, while also avoiding significant degradation in mechanical properties such as elongation and tensile strength, as compared to thermoplastic articles formed from the neat thermoplastic elastomer and subjected to the same heat processing history.

In some embodiments, lubricous thermoplastic articles have a Relative Dynamic COF of less than about 0.9. In other embodiments, lubricous thermoplastic articles have a Relative Dynamic COF of less than about 0.8, or less than about 0.7, or less than about 0.65, or less than about 0.6, or less than about 0.55, or less than 0.5.

In some embodiments, lubricous thermoplastic articles have at least one of a Relative Tensile Strength at Break of greater than about 0.8 and a Relative Elongation at Break of greater than about 0.8. In other embodiments, lubricous thermoplastic articles have at least one of a Relative Tensile Strength at Break of greater than about 0.9, or greater than about 0.95, or greater than about 1, and a Relative Elongation at Break of greater than about 0.9, or greater than about 0.95, or greater than about 1.

For example, in some embodiments, lubricous thermoplastic articles have a Relative Dynamic COF of less than about 0.6, and at least one of a Relative Tensile Strength at Break of greater than about 1 and a Relative Elongation at Break of greater than about 1; and, in other embodiments, lubricous thermoplastic articles have a Relative Dynamic COF of less than about 0.5, and a Relative Tensile Strength at Break of greater than about 1 and a Relative Elongation at Break of greater than about 1.

In some embodiments, lubricious thermoplastic articles have an exterior surface, and the exterior surface is free of any secondary lubricity enhancing agent; that is, any lubricity enhancing agent other than or in addition to the hydrophilic water-insoluble polymer compounded with the thermoplastic elastomer to provide the thermoplastic compounds. Secondary lubricity enhancing agents include any lubricity enhancing agent applied to the lubricious thermoplastic articles as a secondary coating.

In some embodiments, lubricous thermoplastic articles are catheters or other medical devices.

Thermoplastic Elastomer

According to the invention, thermoplastic compounds include thermoplastic elastomer (TPE) selected from thermoplastic polyurethane (TPU), polyether block amide (PEBA), and combinations thereof.

Suitable TPE includes conventional or commercially available TPU and PEBA.

As used herein, the terms "TPU" or "polyurethane" includes polymers containing urethane (also known as carbamate) linkages, urea linkages, amide, or combinations thereof (i.e., in the case of poly(urethane-urea)s). Thus, thermoplastic polyurethanes of the invention contain at least urethane linkages and, optionally, urea or amide linkages.

In general, suitable TPU can be based on aliphatic chemistries or aromatic chemistries. One or more TPU chemistries can be used as the TPU in the thermoplastic compounds of the present invention.

The term "aromatic" refers to TPUs derived from mononuclear aromatic hydrocarbon groups or polynuclear aromatic hydrocarbon groups. The term includes those TPUs derived from arylene groups. The term "arylene group" means a divalent aromatic group.

The term "aliphatic" refers to TPUs derived from saturated or unsaturated, linear, branched, or cyclic hydrocarbon groups. This term is used to encompass those TPUs derived from alkylene (e.g., oxyalkylene), aralkylene, and cycloalkylene (e.g., oxycycloalkylene) groups, for example. The term "alkylene group" means a saturated, linear or branched, divalent hydrocarbon group. Particularly preferred alkylene groups are oxyalkylene groups. The term "oxyalkylene group" means a saturated, linear or branched, divalent hydrocarbon group with a terminal oxygen atom. The term "aralkylene group" means a saturated, linear or branched, divalent hydrocarbon group containing at least one aromatic group. The term "cycloalkylene group" means a saturated, linear or branched, divalent hydrocarbon group containing at least one cyclic group. The term "oxycycloalkylene group" means a saturated, linear or branched, divalent hydrocarbon group containing at least one cyclic group and a terminal oxygen atom.

Non-limiting examples of commercially available TPU include grades of the PELLETHANE brand, such as grade 2363-80AE, available from Lubrizol; and grades of the ELASTOLLAN brand, such as grade 1180A 10, available from BASF. Other commercially available medical grades of TPU also can be used.

In general, PEBA is a block copolymer containing a hard segment of polyamide and a soft segment of polyether.

Non-limiting examples of commercially available PEBA include grades of the PEBAX brand, such as grades 3533 SA01 and 7233, available from Arkema; and grades of the VESTAMID brand available from Evonik. Other commercially available medical grades of PEBA also can be used.

Hydrophilic Water-Insoluble Polymer

According to the invention, thermoplastic compounds include hydrophilic water-insoluble polymer.

Suitable hydrophilic water-insoluble polymer includes polyolefin-polyoxyalkylene block copolymer, crosslinked polyvinylpyrrolidone, and combinations thereof.

While not intending to be limited by theory, it is believed that suitable hydrophilic water-insoluble polymer possesses characteristics, such as certain chemical structure and certain molecular weight, which make it capable of blooming to the surface of a thermoplastic article formed from the thermoplastic compound. It is further believed that, when such blooming occurs, the hydrophilic portion of the hydrophilic water-insoluble polymer becomes available at the surface and thereby provides enhanced lubricity.

Suitable polyolefin-polyoxyalkylene block copolymer includes conventional and commercially available polyolefin-polyoxyalkylene block copolymer.

In some embodiments, the polyolefin-polyoxyalkylene block copolymer is selected from polypropylene-polyoxyethylene block copolymer.

In further embodiments, the polypropylene-polyoxyethylene block copolymer has a molar ratio of polyoxyethylene to polypropylene that is less than about 1:1. For example, in some embodiments, the molar ratio of polyoxyethylene to polypropylene ranges from about 0.6:1 to about 0.9:1.

Non-limiting examples of commercially available polyolefin-polyoxyalkylene block copolymer include grades of the PELESTAT brand, such as grade 300, available from Sanyo. Other commercially available grades of polyolefin-polyoxyalkylene block copolymer also can be used.

Suitable crosslinked polyvinylpyrrolidone includes conventional and commercially available crosslinked polyvinylpyrrolidone, which also may be referred to as crospovidone, crospovidonum, insoluble polyvinylpyrrolidone, and crosslinked PVP.

In some embodiments, the crosslinked polyvinylpyrrolidone is a powder having a particle size distribution wherein at least 95% of particles have a particle size of less than 250 micrometers.

Non-limiting examples of commercially available crosslinked polyvinylpyrrolidone include grades of the KOLLIDON brand, such as grades CL, CL-F, and CL-SF, available from BASF. These different grades of KOLLIDON differ from each other at least in their particles size distributions, bulk densities, and swelling behaviors. Other commercially available grades of crosslinked polyvinylpyrrolidone also can be used.

Optional Other Additives

In some embodiments, thermoplastic compounds include one or more optional additives.

Suitable optional additives include conventional or commercially available plastics additives. Those skilled in the art of thermoplastics compounding, without undue experimentation, can select suitable additives from available references, for example, E. W. Flick, "Plastics Additives Database," *Plastics Design Library* (Elsevier 2004).

Optional additives can be used in any amount that is sufficient to obtain a desired processing or performance property for the thermoplastic elastomer compound and/or the overmolded thermoplastic article. The amount should not be wasteful of the additive nor detrimental to the processing or performance of the thermoplastic elastomer compound and/or the thermoplastic article.

Non-limiting examples of additives suitable for use in the invention include one or more selected from antimicrobial agents; antioxidants and stabilizers; colorants; radiopaque agents; and combinations thereof.

Ranges of Ingredients

Table 1 below shows the acceptable, desirable, and preferable ranges of ingredients for various embodiments of the thermoplastic compounds of the invention in terms of weight percent based on total weight of the thermoplastic compound. Other possible ranges of ingredients for certain embodiments of the disclosed invention are as described elsewhere herein.

Thermoplastic compounds of the disclosed invention can comprise, consist essentially of, or consist of these ingredients. Any number between the ends of the ranges is also contemplated as an end of a range, such that all possible combinations are contemplated within the possibilities of Table 1 as embodiments of compounds for use in the disclosed invention. Unless expressly stated otherwise herein, any disclosed number is intended to refer to both exactly the disclosed number and "about" the disclosed number, such that either possibility is contemplated within the possibilities of Table 1 as embodiments of compounds for use in the disclosed invention.

TABLE 1

| Ranges of Ingredients in the Thermoplastic Compound (wt. %) | | | |
|---|---|---|---|
| | Acceptable | Desirable | Preferable |
| Thermoplastic Elastomer | 55-95 | 65-95 | 75-95 |
| Hydrophilic Water-Insoluble Polymer | 5-20 | 5-20 | 5-20 |
| Optional Other Additives | 0-40 | 0-30 | 0-20 |

The weight percent ranges identified in Table 1 reflect a "fully compounded" thermoplastic compound; that is, one not requiring any dilution with additional thermoplastic polymer resin. Nonetheless, using an expected dilution or "let-down ratio", it is possible to compute a masterbatch or concentrated form of the present invention that can be used to prepare a thermoplastic compound that includes ingredients in the weight percent ranges identified in Table 1. Accordingly, it is possible to form thermoplastic articles from either a fully compounded approach or a masterbatch/let-down approach.

Processing

Preparation of the thermoplastic compounds of the present invention is uncomplicated once the proper ingredients have been selected. The compounds can be made in batch or continuous operations.

Mixing in a continuous process typically occurs in an extruder that is elevated to a temperature that is sufficient to melt the polymer matrix with addition of all additives at the feed-throat, or by injection or side-feeders downstream. Extruder speeds can range from about 200 to about 700 revolutions per minute (rpm), for example, from about 300 rpm to about 600 rpm. Typically, the output from the extruder is pelletized for later processing.

Generally, subsequent preparation of thermoplastic articles of the present invention also is uncomplicated once thermoplastic compounds of the present invention are provided. For example, thermoplastic articles of the present invention can be made by extrusion, injection molding, blow molding, rotational molding, thermoforming, calendering, and the like.

Processing techniques are described in available references, for example, Dominick V. Rosato et al., *Plastics Design Handbook* (Springer 2013).

Methods of Making Thermoplastic Articles

Some aspects of the invention are directed to a method of making lubricious thermoplastic articles.

According to the invention, the method includes the steps of (a) providing ingredients comprising the thermoplastic elastomer and the hydrophilic water-insoluble polymer; (b) melt mixing the ingredients to provide the thermoplastic elastomer compound; and (c) forming the thermoplastic elastomer compound to provide the article for the intended use without a subsequent step of applying a lubricity enhancing agent to the article prior to the intended use.

In some embodiments, the step of forming includes extruding the thermoplastic elastomer compound.

In some embodiments, the intended use includes inserting the lubricious thermoplastic article into a human body.

USEFULNESS OF THE INVENTION

It has been found that, by adding certain of hydrophilic water-insoluble polymer as disclosed herein to thermoplastic elastomer such as thermoplastic polyurethane and polyether block amide to provide thermoplastic compounds, the lubricity of thermoplastic articles formed from the thermoplastic compounds can be enhanced while avoiding significant degradation in mechanical properties such as elongation and tensile strength, as compared to thermoplastic articles formed from the neat thermoplastic elastomer and subjected to the same heat processing history.

Accordingly, thermoplastic compounds of the disclosed invention can be used to make any thermoplastic article that requires enhanced lubricity. Thermoplastic compounds of the disclosed invention are especially useful for making thermoplastic articles for biomedical applications, including but not limited to catheters, tubing, connectors, valves, trocars, and the like.

EXAMPLES

Non-limiting examples of thermoplastic compounds of various embodiments of the disclosed invention are provided.

Table 2 below shows sources of ingredients for the thermoplastic compounds of the Examples.

TABLE 2

| Ingredient Description | Brand | Source |
|---|---|---|
| Thermoplastic polyurethane elastomer | PELLETHANE 2363-80A | Lubrizol |

TABLE 2-continued

| Ingredient Description | Brand | Source |
|---|---|---|
| Thermoplastic polyurethane elastomer | ELASTOLLAN 1180A 10 | BASF |
| Polyether block amide elastomer | PEBAX 3533 SA01 | Arkema |
| Polyether block amide elastomer | PEBAX 7233 | Arkema |
| Polypropylene-polyoxyethylene block copolymer | PELESTAT 300 | Sanyo |
| Crosslinked polyvinylpyrrolidone | KOLLIDON CL-F | BASF |
| Crosslinked polyvinylpyrrolidone | KOLLIDON CL | BASF |
| Crosslinked polyvinylpyrrolidone | KOLLIDON CL-SF | BASF |
| Radiopaque agent | BARIUM SULFATE | Multiple |

Table 3 below show the formulations and certain properties of the Examples 1 to 4.

TABLE 3

| Example | 1 | 2 | 3 | 4 |
|---|---|---|---|---|
| | | Wt. % | | |
| Ingredients | | | | |
| PELLETHANE 2363-80A | 90 | 85 | — | — |
| ELASTOLLAN 1180A 10 | — | — | — | — |
| PEBAX 3533 SA01 | — | — | 90 | 70 |
| PEBAX 7233 | — | — | — | — |
| PELESTAT 300 | 10 | 15 | 10 | 10 |
| KOLLIDON CL-F | — | — | — | — |
| KOLLIDON CL | — | — | — | — |
| KOLLIDON CL-SF | — | — | — | — |
| BARIUM SULFATE | — | — | — | 20 |
| TOTAL | 100 | 100 | 100 | 100 |
| Properties | | | | |
| Hardness (Shore A) | 83 | 84 | 86 | 88 |
| Relative Hardness (unitless) | 0.95 | 0.97 | 1.01 | 1.04 |
| Tensile Strength at Break (psi) | 2932 | 3004 | 1744 | 1622 |
| Relative Tensile Strength at Break (unitless) | 1.07 | 1.10 | 0.89 | 0.91 |
| Elongation at Break (%) | 336 | 461 | 555 | 511 |
| Relative Elongation at Break (unitless) | 1.07 | 1.47 | 1.09 | 0.97 |
| Dynamic COF (unitless) | 0.85 | 0.77 | 0.196 | 0.335 |
| Relative Dynamic COF (unitless) | 0.48 | 0.43 | 0.12 | 0.37 |

Table 4 below show the formulations and certain properties of the Examples 5 to 7.

TABLE 4

| Example | 5 | 6 | 7 |
|---|---|---|---|
| | | Wt. % | |
| Ingredients | | | |
| PELLETHANE 2363-80A | 90 | 90 | — |
| ELASTOLLAN 1180A 10 | — | — | — |
| PEBAX 3533 SA01 | — | — | 90 |
| PEBAX 7233 | — | — | — |
| PELESTAT 300 | — | — | — |
| KOLLIDON CL-F | 10 | — | — |
| KOLLIDON CL | — | 10 | — |
| KOLLIDON CL-SF | — | — | 10 |
| BARIUM SULFATE | — | — | — |
| TOTAL | 100 | 100 | 100 |
| Properties | | | |
| Hardness (Shore A) | 87 | 88 | — |
| Relative Hardness (unitless) | 1.00 | 1.01 | — |

TABLE 4-continued

| Example | 5 | 6 | 7 |
|---|---|---|---|
| | | Wt. % | |
| Tensile Strength at Break (psi) | 2529 | 1711 | — |
| Relative Tensile Strength at Break (unitless) | 0.92 | 0.62 | — |
| Elongation at Break (%) | 554 | 554 | — |
| Relative Elongation at Break (unitless) | 1.76 | 1.76 | — |
| Dynamic COF (unitless) | 0.126 | 0.11 | 0.314 |
| Relative Dynamic COF (unitless) | 0.07 | 0.06 | 0.20 |

Table 5 below show the formulations and certain properties of the Examples 8 to 10.

TABLE 5

| Example | 8 | 9 | 10 |
|---|---|---|---|
| | | Wt. % | |
| Ingredients | | | |
| PELLETHANE 2363-80A | — | — | — |
| ELASTOLLAN 1180A 10 | 75 | — | — |
| PEBAX 3533 SA01 | — | — | 72 |
| PEBAX 7233 | — | 75 | — |
| PELESTAT 300 | — | — | — |
| KOLLIDON CL-F | 5 | 5 | 8 |
| KOLLIDON CL | — | — | — |
| KOLLIDON CL-SF | — | — | — |
| BARIUM SULFATE | 20 | 20 | 20 |
| TOTAL | 100 | 100 | 100 |
| Properties | | | |
| Hardness (Shore A except * = Shore D) | 86 | 70 * | 86 |
| Relative Hardness (unitless) | 1.01 | 1.00 | 1.02 |
| Tensile Strength at Break (psi) | 2697 | 5633 | 2354 |
| Relative Tensile Strength at Break (unitless) | 0.89 | 0.82 | 1.28 |
| Elongation at Break (%) | 601 | 211 | 542 |
| Relative Elongation at Break (unitless) | 1.09 | 0.86 | 1.04 |
| Dynamic COF (unitless) | 0.535 | 0.187 | 0.396 |
| Relative Dynamic COF (unitless) | 0.45 | 0.87 | 0.40 |

Without undue experimentation, those having ordinary skill in the art can utilize the written description, including the Examples, to make and use aspects of the disclosed invention.

All documents cited in the Embodiments of the Invention are incorporated herein by reference in their entirety unless otherwise specified. The citation of any document is not to be construed as an admission that it is prior art with respect to the disclosed invention.

While particular embodiments of the disclosed invention have been illustrated and described, it would be obvious to those skilled in the art that various other modifications can be made without departing from the spirit and scope of the invention. The appended claims are intended to cover all such modifications that are within the scope of the disclosed invention.

What is claimed is:

1. A lubricious thermoplastic article formed from a thermoplastic compound comprising:
   (a) thermoplastic elastomer that is thermoplastic polyurethane; and
   (b) from about 5 to about 20 weight percent, by weight of the compound, of hydrophilic water-insoluble polymer that is crosslinked polyvinylpyrrolidone;
   wherein the crosslinked polyvinylpyrrolidone is a powder having a particle size distribution wherein at least 95% of particles have a particle size of less than 250 micrometers; and
   the crosslinked polyvinylpyrrolidone is crosslinked prior to inclusion into the thermoplastic compound.

2. The article of claim 1, wherein the hydrophilic water-insoluble polymer consists of crosslinked polyvinylpyrrolidone.

3. The article of claim 1, wherein the article has a Relative Dynamic COF of less than about 0.9.

4. The article of claim 3, wherein the article has at least one of a Relative Tensile Strength at Break of greater than about 0.8 and a Relative Elongation at Break of greater than about 0.8.

5. The article of claim 1, wherein the article has a Relative Dynamic COF of less than about 0.6, and wherein the article has at least one of a Relative Tensile Strength at Break of greater than about 1 and a Relative Elongation at Break of greater than about 1.

6. The article of claim 1, wherein the article has a Relative Dynamic COF (Wet) of less than about 0.5, and wherein the article has both a Relative Tensile Strength at Break of greater than about 1 and a Relative Elongation at Break of greater than about 1.

7. The article of claim 1, wherein the thermoplastic compound further comprises one or more additives selected from the group consisting of antimicrobial agents; antioxidants and stabilizers; colorants; radiopaque agents; and combinations thereof.

8. The article of claim 1, wherein the article is a catheter.

9. A method of making the article of claim 1, the method comprising the steps of:
   (a) providing ingredients comprising the thermoplastic elastomer and the hydrophilic water-insoluble polymer;
   (b) melt mixing the ingredients to provide the thermoplastic elastomer compound; and
   (c) forming the thermoplastic elastomer compound to provide the article for the intended use without a subsequent step of applying a lubricity enhancing agent to the article prior to the intended use.

10. The method of claim 9, wherein the step of forming comprises extruding the thermoplastic elastomer compound.

11. The method of claim 9, further comprising the step of inserting the article into a human body.

* * * * *